United States Patent

Kuroda et al.

Patent Number: 5,286,449
Date of Patent: Feb. 15, 1994

[54] ADSORBER MODULE FOR WHOLE BLOOD TREATMENT AND AN ADSORBER APPARATUS CONTAINING THE ADSORBER MODULE

[75] Inventors: Toru Kuroda, Oita; Norio Tohma, Ohno, both of Japan

[73] Assignee: Asahi Medical Co., Ltd., Tokyo, Japan

[21] Appl. No.: 888,313

[22] Filed: May 27, 1992

Related U.S. Application Data

[63] Continuation of Ser. No. 332,973, Apr. 4, 1989, abandoned.

Foreign Application Priority Data

Apr. 4, 1988 [JP] Japan .................. 63-81276

[51] Int. Cl.⁵ .................. A61M 1/14; B01D 13/01
[52] U.S. Cl. .................. 422/48; 210/490; 210/500.23; 435/287; 435/299
[58] Field of Search .......... 422/44, 48; 55/16, 158; 210/490, 500.23; 427/296, 387; 435/2, 287, 299

[56] References Cited

U.S. PATENT DOCUMENTS

| | | | |
|---|---|---|---|
| 4,214,020 | 7/1980 | Ward et al. | 427/296 |
| 4,268,279 | 5/1981 | Shindo et al. | 55/16 |
| 4,576,927 | 3/1986 | Kuroda et al. | 502/402 |
| 4,619,897 | 10/1986 | Hato et al. | 435/182 |
| 4,637,880 | 1/1987 | Halbert | 210/638 |
| 4,729,829 | 3/1988 | Duggins | 210/195.2 |

FOREIGN PATENT DOCUMENTS

| | | |
|---|---|---|
| 0034304 | 8/1981 | European Pat. Off. |
| 0056977 | 8/1982 | European Pat. Off. |
| 0082345 | 6/1983 | European Pat. Off. |
| 0230247 | 7/1987 | European Pat. Off. |
| WO80/02805 | 12/1980 | PCT Int'l Appl. |
| 8002805 | 12/1980 | PCT Int'l Appl. |

Primary Examiner—James C. Housel
Assistant Examiner—N. Bhat

[57] ABSTRACT

A novel adsorber module for whole blood treatment is disclosed, which comprises a casing provided with a blood inlet and a blood outlet and a bundle of a plurality of porous hollow fibers disposed in the casing and disposed between and fluid-tightly connected at end portions thereof to the blood inlet and the blood outlet, wherein each porous hollow fiber comprises a membranous porous resin matrix having pores which open at least at the inner wall of the hollow fiber and a plurality of ligands linked to the overall surface, including the walls of open pores, of the porous resin matrix. The adsorber module can easily be constructed into an adsorber apparatus which can be practically employed for treatment of whole blood. With this apparatus, whole blood can be effectively, efficiently treated without the danger of blood coagulation and hollow clogging, whereby the malignant components of the whole blood can be effectively removed by adsorption on the ligands.

12 Claims, 3 Drawing Sheets

ADSORBER MODULE FOR WHOLE BLOOD TREATMENT AND AN ADSORBER APPARATUS CONTAINING THE ADSORBER MODULE

This application is a continuation of application Ser. No. 07/332,973 filed on Apr. 4, 1989, now abandoned.

BACKGROUND OF THE INVENTION

Field of The Invention

The present invention relates to an adsorber module for whole blood treatment and an adsorber apparatus containing the adsorber module. More particularly, the present invention is concerned with an adsorber module for whole blood treatment comprising a casing provided with a blood introduction means and a blood withdrawal means and a plurality of porous hollow fibers accommodated in the casing, wherein each porous hollow fiber comprises a membranous porous resin matrix having pores which open at least at the inner wall of the hollow fiber and a plurality of ligands linked to the overall surface of the porous resin matrix. Also, the present invention is concerned with an adsorber apparatus comprising the above-mentioned adsorber module, a blood introducing passage means having one end fluid-tightly connected to the blood introduction of the module and a blood withdrawing passage means having one end fluid-tightly connected to the blood withdrawal means of the module.

By the use of the adsorber module and apparatus according to the present invention, it is feasible to accomplish effective, efficient treatment of whole blood without the danger of blood coagulation and hollow clogging so that the malignant components of blood can be effectively removed by adsorption.

Discussion of Related Art

In recent years, as a result of the remarkable progress of medicine (especially internal medicine), hematology, immunology, clinical inspection, etc., various malignant components have been isolated from patient blood and plasma and identified, which are believed to have close relation with the cause and advance of diseases. For example, such malignant components include autoantibodies and immune complexes against autoimmune diseases, such as rheumatoid arthritis, systemic lupus erythematosus, hyperlipemea and the like. Also, such malignant components include low or very low density lipoprotein against familial hyperlipidemia and substances of middle or low molecular weights which are increased by liver diseases.

Accordingly, efforts have been made in the art for developing an advantageous method by which the above-mentioned malignant component can be effectively removed from whole blood to thereby relieve or entirely cure the diseases caused by the component.

The proposals which have hitherto been made in line with the above-mentioned efforts are classified into (1) the one in which use is made of an active carbon or an active carbon having the surface thereof covered with a hydrophilic polymer material to remove the malignant component of plasma from whole blood. (2) the one in which whole blood is separated into a blood cell portion and a plasma portion, followed by removal of the malignant component from the plasma portion using an adsorbent (see, for example, Japanese Patent Application Publication Specification No. 55-22107/1980), and (3) the one in which the plasma separated from whole blood according to a method as mentioned in item (2) above is passed through a filter so as to remove the malignant component of high molecular weight from the plasma (see, for example, Japanese Patent Application Publication Specification No. 63-62/1988).

However, the proposals of items (2) and (3) above have disadvantages in that since separation of plasma from whole blood must be performed prior to adsorption or filtration, complicated apparatus is necessary and the operation is not easily accomplished. Moreover, in these proposals, since the priming volume (total of the inner volumes of apparatus components inclusive of a plasma separator, an adsorber or filter and conduits which are filled with blood) has inevitably been large, the volume of the body fluid taken from a patient has also been large to the detriment of the patient.

The proposals of item (1) above permit simpler apparatus and easier operation than those employed in the proposals in items (2) and (3) above, since whole blood treatment is performed without plasma separation. However, active carbon has poor selectivity for adsorption. Further, the pore size of active carbon is so small that the malignant component of the plasma cannot be adsorbed to a desirable extent.

In addition to the above-described proposals, more recently, it has been proposed to use a flat membrane in which the wall surface (disposed on the outer side relative to the blood path) has bonded thereto an antibody, an antigen, an enzyme or the like to remove the malignant component of plasma, such as an antigen, an antibody, an enzyme, a protein, etc. In this connection, reference is made for example, to PCT Patent Application Publication No. WO 80/02805. However, this proposal has the disadvantage that the adsorbing capacity of the hollow fiber is poor. Moreover, since an unstable biosubstance is used as a ligand in this proposal, sterilization is likely to cause the ligand to have a disadvantageously lowered activity or to cause the ligand to be detached from the fiber, thereby bringing about serious problems with respect to safety.

SUMMARY OF THE INVENTION

With a view toward developing an effective device for removing the malignant component of whole blood which is free from the above-described drawbacks of the prior art, the present inventors have made extensive and intensive studies. As a result, it has unexpectedly been found that a desired device or apparatus for blood treatment can be obtained by the use of porous hollow fibers each comprising a membranous porous resin matrix having pores which open at least at the inner surface of each hollow fiber and a plurality of ligands linked or attached to the overall surface of the porous resin matrix, in which the porous hollow fiber is adapted to allow whole blood to flow within the hollow thereof along the length of the fiber while causing the plasma of the whole blood to contact at least the inner wall surface, including the open pore walls, of each hollow fiber, so that the malignant component of the plasma is adsorbed on the hollow fiber by the interaction between the ligand and the malignant component. Based on this novel finding, the present invention has been completed.

It is, therefore, an object of the present invention to provide an adsorber module by which it is easy to accomplish effective, efficient removal of the malignant component of whole blood without the danger of blood coagulation and hollow clogging so that the malignant components of the blood can be effectively removed by adsorption.

It is another object of the present invention to provide an adsorber module which is not adversely affected by sterilization and can be used in whole blood treatment with safety.

It is a further object of the present invention to provide an adsorber apparatus containing an adsorber of the above character in which the priming volume is small.

It is still a further object of the present invention to provide an adsorber apparatus which is simple is construction and easy in operation.

The foregoing and other objects, features and advantages of the present invention will be apparent to those skilled in the art from the following detailed description and appended claims taken in connection with the accompanying drawings.

BRIEF DESCRIPTION OF THE DRAWINGS

In the drawings:

In FIGS. 1 through 5, like parts or portions are designated by like numerals.

DETAILED DESCRIPTION OF THE INVENTION

In one aspect of the present invention, there is provided an adsorber module for whole blood treatment comprising:

a casing provided with a blood introduction means and a blood withdrawal means, and a plurality of porous hollow fibers substantially equal in length arranged substantially in parallel relationship and bonded together at both end portions thereof to form a bundle, each porous hollow fiber of said bundle having openings at both terminal ends thereof, said bundle being disposed in said casing along the length of said casing, said both end portions of the hollow fibers of said bundle being fluid-tightly connected to said blood introduction means and said blood withdrawal means, respectively, thereby establishing communication between said blood introduction means and said blood withdrawal means through said bundle of hollow fibers, each porous hollow fiber comprising a membranous porous resin matrix having pores which open at least at the inner wall of the hollow fiber and a plurality of ligands attached to the overall surface of said porous resin matrix, said ligands being capable of interacting with a substance to be adsorbed.

Figure 1:
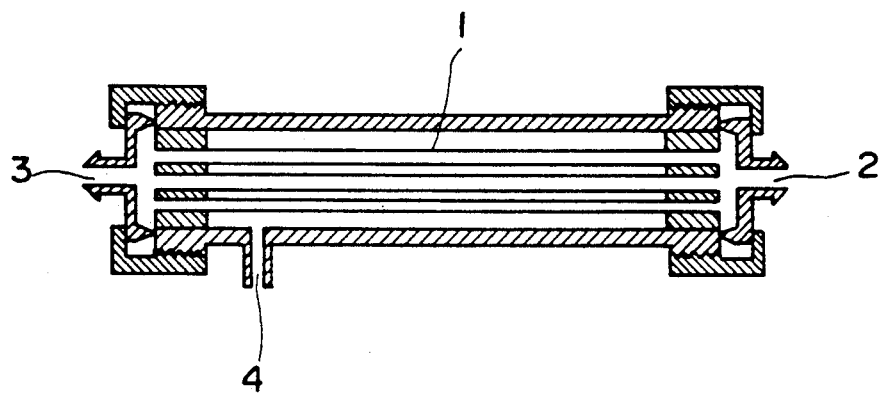
FIG. 1 is a diagrammatic cross-sectional view of one form of an adsorber module according to the present invention.

Referring now to FIG. 1, there is shown a schematic cross-sectional view of one form of adsorber module of the present invention which has opening 4 in the wall of the casing. The adsorber module comprises a casing provided with blood introduction means 2 and blood withdrawal means 3; and a plurality of porous hollow fibers 1 substantially equal in length which are arranged substantially in parallel relationship and bonded together at both end portions thereof to form a bundle. Each porous hollow fiber 1 of the bundle has openings at both terminal ends thereof. The bundle is accommodated in the casing along the length of the casing. The both end portions of hollow fibers 1 of the bundle are fluid-tightly connected to blood introduction means 2 and blood withdrawal means 3, respectively, thereby establishing communication between blood introduction means 2 and blood withdrawal means 3 through the bundle of hollow fibers 1.

The porous hollow fiber employed in the adsorber module of the present invention comprises a membranous porous resin matrix having pores which open at least at the inner wall of the hollow fiber and a plurality of ligands linked or attached to the overall surface of the porous resin matrix. The terminology "overall surface" as used herein means all of the inner and outer surfaces of the hollow fiber membrane and the surfaces defined by the walls of open pores present within the membranous porous resin matrix.

Figure 2:
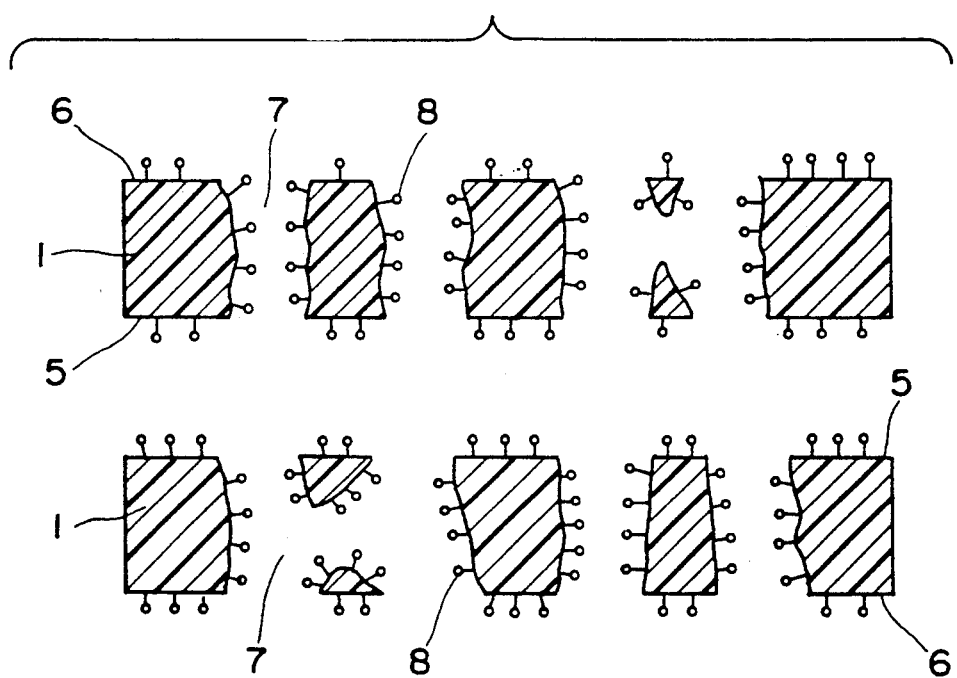
FIG. 2 is an enlarged, diagrammatic cross-sectional view of a portion of a preferred form of hollow fiber used in the present invention, illustrating a plurality of ligands linked to the porous resin matrix of the hollow fiber.

In FIG. 2, there is shown a schematic cross-sectional view of a preferred form of porous hollow fiber used in the present invention. Porous hollow fiber 1 shown in FIG. 1 comprises membranous porous resin matrix (also designated numeral 1 in FIG. 2) and a plurality of ligands 8 linked to the overall surface of the porous resin matrix. The resin matrix 1 has through-paths running between both surfaces 5 and 6 of the resin matrix. As mentioned above, ligands 8 are linked or attached to the overall surface of matrix 1, that is, inner wall surface 5, outer wall surface 6 and pore wall surface 7.

In the present invention, the pores in the resin matrix do not necessarily form through-paths running through the thickness of the resin matrix as long as the pores open at least at the inner wall of the hollow fiber, however, from the viewpoint of attaining efficient, effective removal of the malignant component of whole blood, it is preferred that the membranous porous resin matrix of each hollow fiber have pores therewithin and openings on both surfaces thereof, which pores cooperate with the openings to form through-paths running between both the surfaces of the resin matrix.

The average pore diameter of the porous resin matrix is not particularly limited in the present invention. The pore diameter is generally selected taking into account the size and shape of the malignant component to be removed by the porous hollow fiber membrane. It is preferred that the hollow fiber have a pore diameter at which the plasma containing the malignant component is freely passed through the membrane so that the inner wall surfaces of the pores are so large as to permit unlimited contact of the plasma containing a malignant component with the ligands linked to the porous resin matrix. The average pore diameter is determined as follows. The pore diameter and pore volume of the membrane are measured by means of a mercury porosimeter. The logarithm of the diameter is plotted as the abscissa and the pore volume is plotted as the ordinate to give a pore diameter distribution curve. Thus, the total pore volume is defined by the abscissa and the pore diameter distribution curve. A vertical line can be drawn in parallel to the ordinate so that the total pore volume is halved The value of the pore diameter on the abscissa at its point crossed by the above-mentioned vertical line is referred to as the "average pore diameter" The average pore diameter is generally in the range of from 0.005 to 3 μm, preferably from 0.01 to 2 μm, more preferably from 0.02 to 1 μm.

The area of the overall surface of the porous resin matrix is not critical in the present invention. However, the area of the overall surface is generally at least 5 m²/g, preferably at least 10 m²/g, more preferably at least 15 m²/g. The area of the overall surface is determined as follows. The nitrogen gas adsorption amount of the matrix is measured using a BET (S. Brunauer - P'H. Emmett - E. Taylor) type surface area measuring apparatus, and the overall surface is determined from the nitrogen gas adsorption amount according to the customary one-point method.

In the present invention, it is preferred that the porous hollow fibers have an average effective length (L mm) and an average inner diameter (D mm) which satisfy the inequality:

$$L/D^2 \text{ (mm}^{-1}) \geq 2000.$$

The average effective length is defined as an average of the lengths of the porous hollow fibers minus the lengths of both end portions of the porous hollow fibers which both end portions are bonded together and fluid-tightly connected to blood introduction means 2 and blood withdrawal means 3, respectively.

In the adsorber module of the present invention, each porous hollow fiber is adapted to allow whole blood to flow within the hollow thereof along the length of the fiber while causing the blood to be contacted with the wall surface of each hollow fiber, so that the malignant components of the blood is adsorbed on the hollow fiber by the interaction between the ligands and the malignant components. Since a large surface is effectively utilized for whole blood to be contacted with the ligands linked or attached to surface of the porous resin matrix, effective, efficient removal of the malignant components of whole blood can be attained.

When the membranous porous resin matrix of each hollow fiber have pores therewithin and openings on both surfaces thereof, which pores cooperate with the openings to form through-paths running between both the surfaces of the resin matrix, the volume ratio of erythrocyte to whole blood (hematocrit) is generally higher at portions of the hollow of the porous hollow fiber which are on the side of the blood withdrawal means than at portions of the hollow of the porous hollow fiber which are on the side of the blood introduction means. This is attributed to permeation of the plasma through the wall of the hollow fiber from the inside of the fiber to the outside of the fiber. The above-mentioned increase in the volume ratio of erythrocyte brings about an increase in the viscosity of the blood flowing through the hollow of the porous hollow fiber. The increase in blood viscosity produces an advantageous pressure by which the above-mentioned permeation of blood plasma is promoted. On the other hand, in the adsorber module on the side of the blood withdrawal means, plasma which has been passed through the hollow fiber membrane and has entered the interstices extending between the outer wall of the porous hollow fibers and the inner wall of the casing and between the outer walls of the individual( hollow fibers is returned to the hollow of the porous hollow fiber by the action of the increased pressure of the plasma in the outside of the hollow fiber. The plasma joins the blood having an increased content of erythrocyte in the hollow of the porous hollow fiber, and then the resultant blood is discharged from the adsorber module through the blood withdrawal means. When the plasma first passes from the inside to the outside of the hollow fiber through the hollow fiber wall membrane, a great part of the malignant component is adsorbed. And, when the plasma then passes from the outside to the inside of the hollow fiber through the hollow fiber wall membrane, the malignant component is almost completely removed.

The plasma having most the malignant component removed by first passing it from the inside to the outside of the hollow fiber through the wall membrane, may be discharged from the casing through at least one opening provided for withdrawing the plasma. The plasma discharged from the casing flows through a conduit connected to the opening, and then joins the blood flowing through a conduit which is connected to the blood withdrawal means of the casing, as described later.

From the viewpoint of minimizing the priming volume as well as increasing the malignant component-separating efficiency by the passage of plasma through the hollow fiber membrane, it is preferred that the inner diameter of the porous hollow fiber be as small as possible on the condition that blood can flow through the hollow of the porous hollow fiber. Specifically, the inner diameter of the porous hollow fiber is preferably 100 μm to 1,000 μm, more preferably 150 μm to 400 μm.

In the present invention, it is preferred that the wall thickness of the porous hollow fiber be as large as possible as long as the efficiency for passing plasma through the hollow fiber membrane is not practically impaired. By increasing the wall thickness, the total surface area of the pore wall of the porous hollow fiber is increased. Specifically, the wall thickness of the porous hollow fiber is preferably 10 μm or more, more preferably 50 μm to 500 μm, and most preferably 50 μm to 200 μm.

The membranous porous resin matrix to be used for preparing the present porous hollow fiber may be prepared from a hydrophilic material, such as cellulose, a cellulose derivative, a water-insoluble polyvinyl alcohol and a copolymer of ethylene and vinyl alcohol or a hydrophobic material, such as a polyolefin (e.g., polyethylene or polypropylene), a polysulfone and a polytetrafluoroethylene. It should be noted that when a hydrophobic material is used, since an aqueous solution is not readily passed through a porous hollow fiber made of the hydrophobic material, it is generally necessary to render the surface of the porous hollow fiber hydrophilic, e.g., by coating the surface of the porous hollow fiber with a hydrophilic material or by subjecting the surface of the porous hollow fiber membrane to chemical treatment or plasma treatment.

From the viewpoint of facilitating the linking of the ligands which interact with the malignant component at the surface of the membranous porous resin matrix, it is preferred that the matrix have functional groups to which the ligands are readily bonded, such as a hydroxyl group, an amino group, a carboxyl group and a thiol group. However, since ligands can be linked to the surface of the porous hollow fiber by physical adsorption, embedding, insolubilizing precipitation onto the matrix surface and the like, the porous resin matrix does not necessarily have to possess may such functional groups.

There is no particular limitation with respect to the method for forming a porous hollow fiber. That is, a porous hollow fiber can be formed by a customary method, such as wet spinning, dry spinning, melt spinning or the like. It is preferred to prepare a porous hollow fiber by a stretching perforation method in which a crystalline polymer is spun, e.g., by melt spinning, and subjected to cold stretching to cause cleavage among crystalline lamellae of the polymer and then subjected to hot stretching to attain an expansion of the cleavage. This is because controlling of pore diameters of the porous resin matrix of hollow fiber is easy and because the mechanical strengths of the obtained hollow fiber are high irrespective of the presence of a large number of pores. It is also preferred to prepare a porous hollow fiber from a polyolefin by the stretching perforation method from the viewpoint of the chemical resistance of the matrix of the hollow fiber during the reaction for linking ligands to the surface of the membranous porous resin matrix of hollow fiber.

The ligands may be linked to the surface of the membranous porous resin matrix by any of the customary methods. For example, the ligands are bonded to the surface of the membranous porous resin matrix by, e.g., covalent bonding or ionic bonding. Also, the ligands may be bonded to the surface of the porous matrix by physical adsorption, embedding, insolubilizing precipitation onto the matrix surface or the like. Of these methods, from the viewpoint of avoiding the elution of ligands, it is preferred to use a method in which the ligands are bonded to the surface of the matrix by covalent bonding. Specifically, the conventional carrier activating method and the conventional ligand linking method, which are utilized in the preparation of an immobilized enzyme or in an affinity chromatography, may be employed. Representative examples of carrier activating methods include methods using a cyanogen halogenide, periodic acid, a crosslinking agent or an epoxide. In the carrier activating method, substitution and/or addition of active hydrogen-containing nucleophilic groups, such as an amino group, a hydroxyl group, a carboxyl group and a thiol group, to the reactive groups on the surface of the porous resin matrix is performed by chemical modification with, e.g., a cyanogen halogenide, such as CNBr. However, the carrier activating methods are not restricted to the above-mentioned methods.

"Ligand" used herein means a substance which selectively interacts with a malignant component to be adsorbed on the hollow fiber, which is contained in blood plasma.

Representative examples of ligands include an amino acid, a peptide, a protein, a glycoprotein, a monosaccharide, an oligosaccharide, a polysaccharide, a lipid, an antigenic substance, a nucleic acid, a nonprotein organic compound and an inorganic compound. Representative examples of proteins and glycoproteins include an antibody, a complement, a protein relating to blood coagulation and an enzyme.

However, it is preferred that the ligands exhibit no or only weak antigenicity and toxicity even if it is eluted into blood, and that when the ligands are in contact with blood corpuscles, the ligands do not cause hemolysis of erythrocyte, sensitization of leukocyte or adherence and/or aggregation of platelet. In this connection, when a peptide, a protein and a glycoprotein have a low weight average molecular weight, they have a low antigenicity. Therefore, with respect to a peptide, a protein and a glycoprotein, it is preferred that they have a low weight average molecular weight, although there is generally no particular restriction with respect to the molecular weight of the ligands. From these viewpoints, preferred are a peptide, a protein and a glycoprotein, each of which has a preferred weight average molecular weight of not greater than $10^4$; and a monosaccharide, an oligosaccharide, a polysaccharide, a lipid, a nucleic acid, a nonprotein organic compound (e.g., a polyanion), an inorganic compound, an amino acid and a peptide each having a weight average molecular weight of not greater than $10^3$. The weight average molecular weight of the peptide, the protein and the glycoprotein are determined by measuring a sedimentation coefficient of the solute. That is, the sedimentation coefficient of the peptide, the protein or the glycoprotein is measured according to the sedimentation velocity method using an ultracentrifuge, and the molecular weight is calculated by substituting the sedimentation coefficient measured for the s in the following Svedberg formula:

$$\text{Weight average molecular weight } (Mw) = \frac{R \cdot T \cdot s}{D(1 - \bar{v}\rho)}$$

wherein R represents the gas constant, T represents the absolute temperature, s represents the sedimentation coefficient of a solute, D represents the diffusion coefficient of a solute, $\bar{v}$ represents the partial specific volume of a solute and $\rho$ represents the density of a solvent.

Representative examples of ligands are as follows.

For the treatment of systemic lupus erythematosus, preferable use is made of a mononucleoside containing adenine, guanine, cytosine, uracil or thymine, an oligonucleoside or polynucleoside comprising such a mononucleoside; and a natural nucleic acid, such as DNA and RNA. These are used to remove an antinuclear antibody and an anti-DNA antibody which are present in blood plasma. Further, a basic compound, such as actinomycin D, may be used to remove DNA, RNA and ENA which are present in blood plasma.

For the treatment of the so-called immune complex diseases, such as chronic articular rheumatism, malignant tumor and systemic lupus erythematosus, a hydrophobic compound may be used to remove an immune complex.

For the treatment of diseases so-called autoimmune diseases, such as myasthenia, multiple sclerosis and chronic articular rheumatism, a hydrophobic compound may be used to remove an autoantibody.

For the treatment of hyperlipemia, use is preferably made of a polyanion, e.g., an acid polysaccharide, such as heparin and dextran sulfate; a synthetic polyanion, such as polyvinyl sulfate and polyacrylic acid. These are used to remove a low density lipoprotein and a very low density lipoprotein.

The ligands to be used in the present invention are not restricted to the above-mentioned ones. The ligands may be used individually or in combination.

When the ligands are used in combination, the bundle to be incorporated in the present adsorber module may be comprised of hollow fibers of the same kind, each having different types of ligands or of different hollow fibers which are different in the type of ligand linked thereto.

With respect to a hydrophobic compound and a polyanion used as ligands, a more detailed explanation will be made as follows.

The hydrophobic compound to be used in the present invention is a compound having a solubility in physiological saline of not greater than 100 mmole/dl (at 25° C.), preferably not greater than 30 mmole/dl (at 25° C.). When a compound having a solubility exceeding 100 mmole/dl in physiological saline is used, the compound is so hydrophilic that the compound has poor affinity for an autoantibody and an immune complex, thereby leading to an extreme lowering in the adsorbing capacity of the adsorber module. Further, since such a compound has an affinity for an albumin which is hydrophilic, the albumin is likely to be non-selectively adsorbed on the porous hollow fiber. This is disadvantageous.

When a hydrophobic compound having at least one aromatic ring is used as the ligand, particularly preferable results can be obtained. A hydrophobic compound having any type of aromatic ring may be advantageously used. However, it is preferred to use a hydrophobic compound having at least one aromatic ring selected from a benzene type aromatic ring, such as a benzene ring, a naphthalene ring and a phenanthrene ring; a nitrogen-containing six-membered ring, such as a pyridine ring, a quinoline ring, an acridine ring, an isoquinoline ring and a phenanthridine ring; a nitrogen-containing five-membered ring, such as an indole ring, a carbazole ring, an isoindole ring, an indolizene ring, a porphyrin ring and 2,3,2',3'-pyrrolopyrrole ring; a six-membered ring having 2 or more nitrogen atoms, such as a pyridazine ring, a pyrimidine ring, a symtriazine ring, a sym-tetrazine ring, a quinazolin ring, a 1,5-naphthyridine ring, a pteridine ring and a phenazine ring; a five-membered ring having 2 or more nitrogen atoms, such as a pyrazole ring, a 1,2,4-triazole ring, a 1,2,3-triazole ring, a tetrazole ring, a benzimidazole ring, an imidazole ring and a purine ring; an oxygen-containing aromatic ring, such as a norharman ring, a perimidine ring, a benzofuran ring, an isobenzofuran ring, and dibenzofuran ring; a sulfur-containing aromatic ring, such as a benzothiophene ring, a thienothiophene ring and a thiepine ring; an oxygen-containing heterocyclic aromatic ring, such as, an oxazole ring, an isooxyzole ring, a 1,2,5-oxadiazole ring and a benzoxazole ring; a sulfur-containing heterocyclic aromatic ring, such as a thiazole ring, an isothiazole ring, a 1,3,4-thiadizaole ring and a benzothiazole ring; and derivatives thereof. Of these compounds, a compound having an indole ring, such as tryptamine, provides particularly preferred results. This is probably because the hydrophobic nature and rigidity of the molecule of such compounds promote the bonding of the compounds with an autoantibody and an immune complex.

It has been found that a hydrophobic amino acid and a derivative thereof which are practically harmless and inexpensive are extremely advantageous to remove an autoantibody and an immune complex. The hydrophobic amino acid and a derivative thereof preferably have a hydrophobic parameter of 1500 cal/mol or more, which hydrophobic parameter is defined by Tanford and Nozaki in Journal Of American Chemical Society 184, page 4240 (1962) and Journal Of Biological Chemistry 246, page 2211 (1971). Also, the hydrophobic amino acid and a derivative thereof preferably have a solubility in physiological saline of 100 mmole/dl or less (at 25° C.). When the solubility exceed 100 mmole/dl, the hydrophobic interaction between the hydrophobic amino acid and a derivative thereof and a malignant component becomes weak, thereby causing the adsorber module to have poor adsorbing ability.

Representative examples of hydrophobic amino acids and derivatives thereof include lysine, valine, leucine, tyrosine, phenylalanine, isoleucine, tryptophan and derivatives thereof.

Of these hydrophobic amino acids and derivatives thereof, phenylalanine, tryptophan and derivatives thereof are particularly preferred. There is no particular limitation with respect to the optical isomerism of the hydrophiblic amino acid. That is, the hydrophobic amino acid may be dextrorotatory or levorotatory.

The weight average molecular weight of the hydrophobic compound to be used in the present invention is preferably 10,000 or less, more preferably 1,000 or less. The weight average molecular weight of the hydrophobic compound is determined in substantially the same manner as in the measurement of the weight average molecular weights of the peptide, the protein and the glycoprotein. When the hydrophobic compound has the above-mentioned preferable weight average molecular weight, the hydrophobic compound is readily linked to the membranous porous resin matrix of hollow fiber, and the hydrophobic compound-linked porous hollow fiber has good storage stability as compared to that of a natural polymer, such as protein S (weight average molecular weight: 42,000). Even if a hydrophobic compound having a weight average molecular weight of 10,000 or less is eluted from a porous hollow fiber into blood, since the antigenicity of the hydrophobic compound is negligibly low, there arises no safety problem for a living body. The hydrophobic compound having a weight average molecular weight of 10,000 or less is not deactivated by sterilization.

The term "polyanion" used herein means a polymer which has a weight average molecular weight of 600 or more and which has functional groups capable of producing a negative charge in a body fluid, such as a sulfonic group, a carboxyl group and a phosphoric group. The weight average molecular weight of the polyanion is determined in substantially the same manner as in the measurement of the weight average molecular weights of the peptide, the protein and the glycoprotein. The polyanion is preferably in the form of a straight chain polymer so as to capture a malignant component effectively. The weight average molecular weight of the polyanion is preferably in the range of 600 to $10^7$, more preferably 1,000 to $5 \times 10^6$, most preferably $2,000 \times 10^6$. Since a low density lipoprotein and a very low density lipoprotein, which are malignant components, have a diameter as large as $2 \times 10^{-4}$ to $8 \times 10^{-4}$ μm, it is desired to use a polyanion having the above-mentioned weight average molecular weight. When the polyanion has a weight average molecular weight of less than 600, the adsorbing capacity for a low density lipoprotein and a very low density lipoprotein is likely to be insufficient. It is preferred that the polyanion have at least one of the above-mentioned functional groups capable of producing a negative charge in a body fluid, such as a sulfonic group, a carboxylic group and a phosphoric group per 300, more preferably per 200, most preferably per 50 to 150 in weight average molecular weight of the polyanion. This is because strong electrostatic interaction can be attained between the polyanion and a malignant component. This weight average molecular weight of the polyanion means a weight average molecular weight which includes the molecular weight of the functional groups.

Representative examples of polyanions include vinyl type synthetic polyanions, such as a polyacrylic acid, a polymethacrylic acid, a polyvinyl sulfonic acid, a polyvinyl sulfuric acid, a polymaleic acid, polyfumaric acid and derivatives thereof: styrene type synthetic polyanions, such as a poly(styrenesulfonic acid) and a poly(styrenephosphoric acid); peptide type polyanions, such as a polyglutamic acid and a polyaspartic acid; nucleic acid type polyanions, such as a poly U and a poly A; synthetic polyanions, such as a polyphosphoric acid ester, a poly-α-methylstyrenesulfonic acid and copolymers of styrene and methacrylic acid; and polysaccharide type polyanions, such as heparin, dextran sulfate, chondroitin sulfate, alginic acid, pectin, hyaluronic acid and derivatives thereof. However, the polyanoin to be used in the present invention is by no means restricted to the above-mentioned specific examples.

The ligands capable of interacting with a malignant component are linked to the overall surface of a membranous porous resin matrix, preferably with substantially uniform distribution. However, in some portions, the ligands may be non-uniformly linked to the surface of the membranous porous resin matrix. Further, in the surface of a membranous porous resin matrix, there may be present some portions to which the ligands are not linked, as long as the presence of such portions cause little adverse effect on the adsorbing capacity for a malignant component.

The distribution of the ligands linked to the inner wall surface and the outer wall surface of the membranous porous resin matrix can be observed by coloring the ligands according to the customary staining method. The distribution of the ligands linked to the wall surface of the pores of the porous resin matrix can be observed by immersing the porous fiber in an aqueous solution of a metal salt to form a salt of the ligand with the metal utilizing the interaction between the ligand and the metal, cutting off a thin section from the resultant porous fiber and subjecting the thin section to observation using an X-ray micro analyzer to detect the metal which is present in the form of the salt of the ligand with the metal linked to the wall of the pores of the porous fiber.

When the inner surface of the porous hollow fiber is subjected to treatment for prevention of hollow clogging by platelets and/or treatment for prevention of blood coagulation, more preferable results are obtained.

The porous hollow fibers are packed in a casing to prepare the adsober module for blood treatment according to the present invention by the use of a customary method, e.g., a method for preparing an artificial kidney.

The adsober module for whole blood treatment of the present invention can advantageously be constructed into an adsorber apparatus.

Accordingly, in another aspect of the present invention, there is provided an adsorber apparatus for whole blood treatment comprising:

(a) an adsorber module comprising:
a casing provided with a blood introduction means and a blood withdrawal means, and
a plurality of porous hollow fibers substantially equal in length arranged substantially in parallel relationship and bonded together at both end portions thereof to form a bundle, each porous hollow fiber of said bundle having openings at both terminal ends thereof,
the bundle being disposed in the casing along the length of the casing,
the both end portions of the hollow fibers of the bundle being fluid-tightly connected to the blood introduction means and the blood withdrawal means, respectively, thereby establishing communication between the blood introduction means and the blood withdrawal means through the bundle of hollow fibers,
each porous hollow fiber comprising a membranous porous resin matrix having pores which open at least at the inner wall of the hollow fiber and a plurality of ligands attached to the overall surface of said porous resin matrix,
the ligands being capable of interacting with a substance to be adsorbed, (b) a blood introducing passage means comprising a first conduit having one end fluid-tightly connected to the blood introduction means of module (a), a second conduit having a blood inlet at one end thereof, and a blood transport means disposed between and fluid-tightly connected to the other ends of the first and second conduits; and (c) a blood withdrawing passage means comprising a third conduit having one end fluid-tightly connected to the blood withdrawal means of module (a) and having a blood outlet at the other end thereof.

In the adsorber apparatus, preferably, the membranous porous resin matrix of each hollow fiber of the adsorber module may have pores therewithin and openings on both surface thereof, which pores cooperate with the openings to form through-paths running between both the surfaces of the resin matrix. In this case, the casing of module (a) may further be provided with at least one opening for withdrawing the plasma which opening is fluid-tightly connected to the blood withdrawing passage means through a bypass comprising a fourth conduit having one end fluid-tightly connected to the opening, a fifth conduit having one end fluid-tightly connected to the blood withdrawing passage at its intermediate position, and a plasma transport means disposed between and fluid-tightly connected to the other ends of the fourth and fifth conduits.

Figure 3:
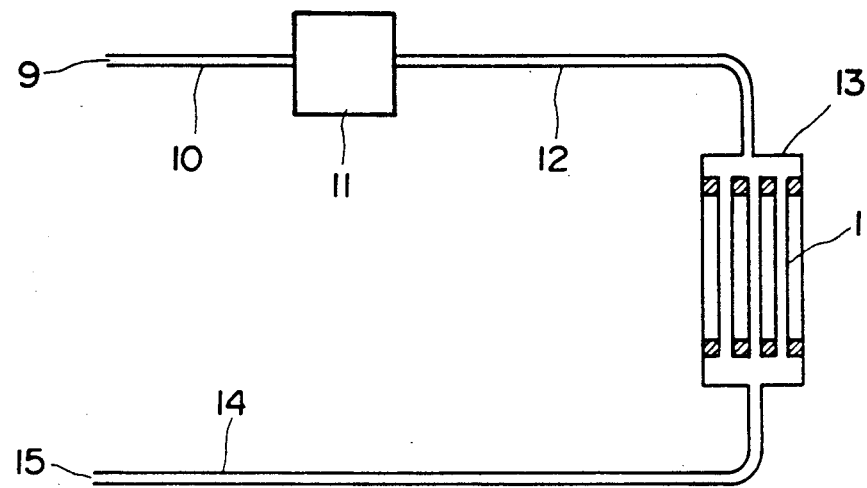
FIG. 3 is a diagrammatic view of one form of an adsorber apparatus according to the present invention.

Referring to FIG. 3, there is shown one form of adsorber apparatus of the present invention. The apparatus comprises (a) adsorber module 13 having no opening (as indicated in FIG. 1) in the casing for withdrawing the plasma; (b) a blood introducing passage means comprising first conduit 12 having one end fluid-tightly connected to module 13 at its blood introduction means 2 (not shown), second conduit 10 having blood inlet 9 at one end thereof, and blood transport means 11 (e.g., pump) disposed between and fluid-tightly connected to the other ends of first and second conduits 12 and 10; and (c) a blood withdrawing passage means comprising third conduit 14 having one end fluid-tightly connected to module 13 at its blood withdrawal means 3 (not shown) and having blood outlet 15 at the other end thereof. Each porous hollow fiber 1 of module 13 is adapted to allow whole blood, which is introduced from blood inlet 9 through the blood introducing passage, to flow within the hollow thereof along the length of fiber 1 while causing the plasma of the blood to be contacted at least inner wall surface 5, including open pore walls, of each hollow fiber 1, so that the malignant component of the plasma is adsorbed on hollow fiber 1 by the interaction between ligand 8 and the malignant component.

In operation, whole blood is introduced to the adsorber apparatus from the patient (donor) through blood inlet 9 and flowed to adsorber module 13 at a predetermined flow rate through conduits 10 and 12 by means of blood transport means 11 (e.g., pump). The whole blood is treated during the flowing through the hollow fibers so that the malignant components of the blood are adsorbed on the ligands attached to the hollow fiber membranes. The blood treated with the adsorber module 13 is flowed through conduit 14 and returned to the donor through blood outlet 15. The whole blood from the donor is recycled through the same absorber apparatus. The recycling is continued for a predetermined period of time. After the recycling purified, the whole blood of the patient becomes pure.

It is preferred that the membranous porous resin matrix of each hollow fiber 1 of adsorber module 13 have pores therewithin and openings on both surfaces and thereof, which pores cooperate with the openings to form through-paths running between both surfaces and of the resin matrix. When such hollow fibers are used in adsorber module 13, during the flowing of the whole blood through the hollows of the hollow fibers, the plasma permeates through the wall of each hollow fiber from the inside of the fiber to the outside of the fiber. The plasma which has been passed through the hollow fiber membrane and has entered the interstices extending between the outer wall of the porous hollow fibers and the inner wall of the casing and between the outer walls of the individual hollow fibers is returned to the hollow of the porous hollow fiber by the action of the increased pressure of the plasma in the outside of the hollow fiber. This is advantageous from the viewpoint of attaining a greater contact area between the whole blood and the ligand.

Figure 4:
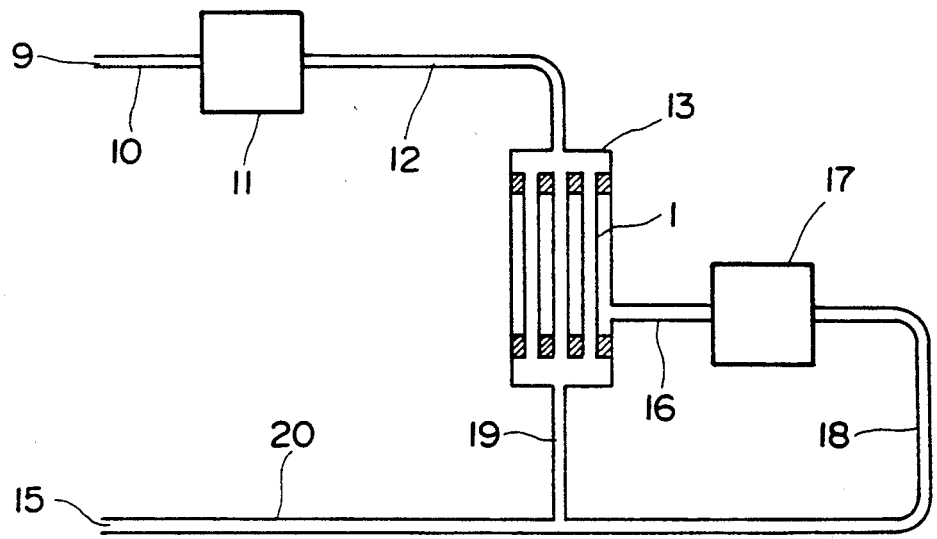
FIG. 4 is a diagrammatic view of another form of an adsorber apparatus according to the present invention.

Referring to FIG. 4, there is shown another form of the adsorber apparatus of the present invention. In adsorber module 13, as described with reference to FIG. 2, the membranous porous resin matrix of each hollow fiber 1 of adsorber module 13 has pores 7 therewithin and openings on both surfaces 5 and 6 thereof, which pores 7 cooperate with the openings to form through-paths running between both surfaces 5 and 6 of the resin matrix. Therefore, as described above, when the whole blood is allowed to flow within the hollows along fibers 1, the plasma of the blood is caused to be selectively passed from the inside to the outside and, in turn, from the outside to the inside of each hollow fiber 1 reciprocally through the walls of hollow fibers 1. In the apparatus of FIG. 4, the casing of adsorber module 13 is further provided with at least one opening for withdrawing the plasma. The opening is fluid-tightly connected to blood withdrawing passage means (19 and 20) through a bypass comprising fourth conduit 16 having one end fluid-tightly connected to the opening, fifth conduit 18 having one end fluid-tightly connected to blood withdrawing passage (19 and 20) at its intermediate position, and plasma transport means 17 (e.g., pump) disposed between and fluid-tightly connected to the other ends of fourth and fifth conduits 16 and 18.

In operation, whole blood is introduced in the adsorber apparatus from blood inlet 9 and flowed to adsorber module 13 at a predetermined rate through conduits 10 and 12 by means of blood transport means 1 (e.g., pump). In adsorber module 13, the blood is allowed to flow through the hollows of hollow fibers 1, and the plasma of the blood is allowed to pass through the membrane of each hollow fiber. The thus separated, purified plasma is flowed to conduit 20 through a bypass, i.e., through conduits 16 and 18 by means of blood transport means 17 (e.g., pump) at a flow rate which is lower than the flow rate of the blood flowing from conduits 10 and 12 into adsorber module 13 by means of pump 11. On the other hand, the cell-enriched blood which has not been passed through the bypass is flowed to conduit 20 through conduit 19. In conduit 20, the purified plasma is combined with the cell-enriched blood and the resultant mixture is returned to the donor through blood outlet 15. The blood from the patient is recycled through the same adsorber apparatus. The recycling is continued for a predetermined period of time. After the recycling, the whole blood of the patient becomes pure.

As described, the adsorber module of the present invention can easily be constructed into an adsorber apparatus which can be practically employed for treatment of whole blood. With this apparatus, whole blood can be effectively, efficiently treated without the danger of blood coagulation and hollow clogging, whereby the malignant components of the whole blood can be effectively removed by adsorption.

As described above, the adsorber module and the adsorber apparatus of the present invention is very effective for the treatment of whole blood, but they also can be effectively used for removing the malignant components of plasma separated from whole blood by means of a conventional plasma separator.

DETAILED DESCRIPTION OF THE PREFERRED EMBODIMENTS

The present invention will now be described in more detail with reference to the following Examples, which should not be construed to be limiting the scope of the present invention.

EXAMPLE 1

A high-density polyethylene (HI-ZEX 2208J, a product of Mitsui Petrochemical Co., Japan) having a density of 0.968 g/cm$^3$ and a melt index, as measured in accordance with ASTM D1238, of 5.5 is extruded from an annular hollow fiber spinning nozzle having an annular orifice outside diameter of 35 mm and an annular orifice inside diameter of 27 mm (slit width: 4 mm) at a winding temperature of 150° C. and at a polymer extrusion rate of 16 g/min and a winding rate of 200 m/min. The thus obtained hollow fiber is subjected to annealing at 115° C. for 2 hours. The annealed hollow fiber is then cold-stretched at room temperature at a stretching ratio (times) (the ratio of the length of the stretched hollow fiber to the length of the hollow fiber before stretching, expressed by times) of 1.33 times by passing the annealed hollow fiber through stretching rolls arranged to provide a stretching path of 200 mm. Then, the cold-stretched hollow fiber is hot-stretched successively at 78° C., 95° C. and 98° C. at stretching ratios at 78° C., 95° C. and 98° C. of 3 times, 1.28 times and 1.14 times, respectively. The ratio (%) of the length of the stretched hollow fiber to the original length of the hollow fiber before cold-stretching and hot-stretching is 480%. The thus stretched hollow fiber is heat set at 115° C. for 2 min, to thereby obtain a porous polyethylene hollow fiber.

The polyethylene hollow fiber is immersed in a solution of polyethylene vinyl alcohol (Soanol Z, manufactured and sold by The Nippon Synthetic Chemicals Industry Co., Ltd., Japan) in 70% (w/w) aqueous ethanol solution, having a polyethylene vinyl alcohol concentration of 0.9% by weight, and kept at 50° C. for 5 min in the solution. Then, the hollow fiber is taken out of the solution and dried at 55° C. for 1.5 hours. The resultant hollow fiber has an inside diameter of 340 $\mu$m, an outside diameter of 440 $\mu$m, a membrane thickness of 50 $\mu$m, an average pore diameter of 0.3 $\mu$m and a surface area of 21 m$^2$/g.

The hollow fiber is cut to the length of 30 cm to obtain 2000 cut hollow fibers, and they are immersed in a mixture of 500 ml of acetone, 390 ml of epichlorohydrin and 90 ml of a 40% (w/w) aqueous NaOH solution. The hollow fibers are subjected to ultrasonication in the mixture at 30° C. for 5 hours. Thereafter, the hollow fibers are washed with acetone and then with water, to obtain epoxy-activated polyethylene hollow fibers.

The epoxy-activated polyethylene hollow fibers are immersed in 1000 ml of 1M sodium carbonate buffer (pH 9.8) containing 10.20 g of tryptophan and subjected to ultrasonication at 50° C. for 24 hours, to thereby link tryptophan to the overall surface of each of the hollow fibers. The amount of tryptophan linked as a ligand to the surface of each of the hollow fibers is 360 $\mu$mol/g (dry basis). The ligand-linked hollow fibers are dried. The dried hollow fibers are inserted in a polyethylene-made cylindrical casing so that they are arranged substantially in parallel relationship and accommodated in the casing along the length thereof. Then, both end portions of the hollow fibers and both end portions of the inner side wall of a polycarbonate-made cylindrical casing having a plasma outlet on its side wall are bonded by a centrifugal molding method using a polyurethane resin adhesive to obtain an assembly. Both the end portions of the resultant assembly are cut off to open the terminals of the hollow fibers, and an opening-having end cap is then attached to each of the end portions of the assembly as shown in FIG. 1 to provide a blood introduction means and a blood withdrawal means so that the both end portions of the hollow fibers are fluid-tightly connected to the blood introduction means and the blood withdrawal means, respectively, thereby establishing communication between the blood introduction means and the blood withdrawal means through the hollow fibers. Thus, there is obtained an adsorber module as shown in FIG. 1. The average effective length of the hollow fibers of the adsorber module is 255 mm, and the ratio of the effective length of the hollow fiber to the square of the inside diameter of the hollow fiber $(L/D^2) = 2206$ mm$^{-1}$.

Using the adsorber module, an adsorber apparatus for whole blood treatment as shown in FIG. 4 is constructed.

A blood from a patient suffering from rheumatoid arthritis is heparinized. An aliquot of the blood is subjected to measurement of amounts of rheumatoid factor, immune complex and platelet. The measurement of the amount of rheumatoid factor is conducted by a passive hemagglutination test method using a RAHA test kit (manufactured and sold by Fuji Zoki Pharmaceutical Co., Ltd., Japan), and the measurement of the amount of immune complex is conducted by a Raji Cell method as described in "Immune Complex Disease", 1st ed., published by Ishiyaku Publishers, Inc., Tokyo, Japan (1982), pp. 93-94. The measurement of the amount of platelet is conducted by a well known Brecher-Cronkite method in which a blood sample is diluted 100 times with a 1% aqueous ammonium oxalate solution and subjected to measurement of the platelet concentration by using a hemocytometer. The blood is introduced to the adsorber apparatus from the patient (donor) through blood inlet 9 and flowed to adsorber module 13 at a flow rate of 50 ml/min through conduits 10 and 12 by means of pump 11 (blood transport means). In adsorber module 13, the blood is allowed to flow through the hollows of hollow fibers 1, and the plasma of the blood is allowed to pass through the membrane of each hollow fiber. The thus separated plasma is flowed to conduit 20 through a bypass, i.e., through conduits 16 and 18 by means of pump 17 at a flow rate of one third of the flow rate of the blood flowed into adsorber module 13 by means of pump 11. On the other hand, the cell-enriched blood which has not been passed through the bypass is flowed to conduit 20 through conduit 19. In conduit 20, the plasma is combined with the cell-enriched blood and the resultant mixture is returned to the donor through blood outlet 15. The blood from the donor is recycled through the same adsorber apparatus. The recycling is continued for 30 min. With this adsorber apparatus, recycling of the blood is stably, sufficiently performed using an extracorporeal circuit blood volume as small as 210 ml. This volume is satisfactorily small from the viewpoint of attaining the whole blood treatment with a decreased extracorporeal circuit blood volume being taken outside the body.

The blood treatment by the adsorber apparatus can be stably conducted without blood coagulation and hemolysis.

After the blood recycling for 30 min, an aliquot of the recycled blood is collected from blood outlet 20 and the amounts of rheumatoid factor, immune complex and platelet in the blood collected are measured in the same manner as mentioned above.

As a result, it is found that the amounts of the rheumatoid arthritis and immune complex before the blood treatment which are 1280 and 120 $\mu$g/ml, respectively, are decreased to 320 and 28 $\mu$g/ml, respectively, after the blood treatment.

On the other hand, the platelet concentration before the treatment is 340,000 cells/mm$^3$, while the platelet concentration after the treatment is 300,000 cells/mm$^3$. That is, the platelet concentration is not so lowered by the whole blood treatment.

As apparent from the above, by the use of the adsorber apparatus of the present invention, malignant substances (i.e., rheumatoid factor and immune complex) are selectively removed with little loss of platelets.

EXAMPLE 2

Epoxy-activated hollow fibers are prepared in the same manner as in Example 1, and immersed in a 30% (w/w) aqueous dextran sulfate solution (pH 13) and kept at 50° C. for 24 hours, to thereby link dextran sulfate (a ligand) to the overall surface of each hollow fiber. The resultant hollow fibers are sufficiently washed with water. Using the washed hollow fibers, an adsorber module is prepared in the same manner as in Example 1.

Then, using the thus obtained adsorber module, an adsorber apparatus for blood treatment is constructed as shown in FIG. 3.

A blood from a patient suffering from familial hypercholesterolemia and having a hematocrit (Ht) of 35% is heparinized. An aliquot of the blood is subjected to measurement of the total cholesterol concentration and platelet concentration. The measurement of total cholesterol concentration is conducted by an enzyme assay using a test kit Cholesterol C-Test Wako, manufactured and sold by Wako Pure Chemicals Industries Ltd., Japan. The most part of cholesterol present in the blood of a patient of familial hypercholesterolemia is derived from low-density lipoproteins, and the term "total cholesterol" means to include cholesterol and low-density lipoproteins. The measurement of platelet concentration is conducted in the same manner as in Example 1. The blood is introduced to the adsorber apparatus from the patient (donor) through blood inlet 9 and flowed to adsorber module 13 at a flow rate of 50 ml/min through conduits 10 and 12 by means of pump 11. 10 Minutes later, it is observed that the interstices extending between the casing and the hollow fibers of the adsorber module and between the outer surfaces of individual hollow fibers have been filled with plasma assuming light yellow. The blood treated with the adsorber module is returned to the donor through blood outlet 15. The blood from the donor is recycled through the same absorber apparatus in the same manner as in Example 1. The recycling is continued for 30 minutes. With this adsorber apparatus, recycling of the blood is stably, sufficiently performed using an extracorporeal circuit blood volume as small as 160 ml. This volume is satisfactorily small from the viewpoint of attaining the whole blood treatment with a decreased extracorporeal circuit blood volume being taken outside the body. 30 Minutes later, an aliquot of the recycled blood is collected from blood outlet 15 and the total cholesterol concentration of the collected blood is measured according to the same method as mentioned above. As a result, it is found that the total cholesterol concentration is decreased to 110 mg/dl after the blood treatment, which is extremely low as compared to the total cholesterol concentration of the blood before the blood treatment, that is, 540 mg/dl.

On the other hand, the platelet concentration of the blood is also determined after the blood treatment. As a result, it is found that the platelet concentration after the blood treatment is 250,000 cells/mm$^3$, while the platelet concentration before the blood treatment is 270,000 cells/mm$^3$. That is, the platelet concentration is not so lowered by the blood treatment.

As apparent from the above, by the use of the adsorber apparatus of the present invention, a malignant substances (i.e., cholesterol and low-density lipoproteins) are selectively removed with little loss of platelets.

EXAMPLES 3 to 5

A high-density polyethylene (HI-ZEX 2208J, a product of Mitsui Petrochemical Co., Japan) having a density of 0.968 g/cm$^3$ and a melt index, as measured in accordance with ASTM D1238, of 5.5 is extruded through a spinning nozzle having an annular orifice outside diameter of 33 mm and an annular orifice inside diameter of 25 mm at a winding temperature of 150° C., and at a polymer extrusion rate of 16 g/min and a winding rate as shown in Table 1. The thus obtained hollow fiber is subjected to annealing at 115° C. for 2 hours. The annealed hollow fiber is then cold-stretched at room temperature at a stretching ratio (times) (the ratio of the length of the stretched hollow fiber to the length of the hollow fiber before stretching, expressed by times) of 1.33 times by passing the hollow fiber through stretching rolls arranged to provide a stretching-path of 200 mm. Then, the cold-stretched hollow fiber is hot-stretched successively at 78° C., 95 ° C. and 98° C. to thereby stretch the hollow fiber at a ratio (%) of the length of the hollow fiber to the original length of the hollow fiber before cold-stretching and hot-stretching, of 480%. The resultant hollow fiber is heat set at 115° C. for 2 min, to thereby obtain a porous polyethylene hollow fiber.

The polyethylene hollow fiber is subjected successively to polyvinyl alcohol-treatment, epoxy-activation, and treatment for linking ligands in the same manner as in Example 1. Then, an adsorber module for blood treatment is prepared using the porous polyethylene hollow fiber in the same manner as in Example 1. The average inside diameter (D), the average effective length (L) and the total surface area of the hollow fibers in the adsorber module are shown in Table 1. Using the adsorber module, substantially the same adsorber apparatus for blood treatment as shown in FIG. 4 except that a plasma circuit including pump 17 and conduit 18 is removed, and a container is attached to conduit 16 in order to collect plasma separated by adsorber module 13 is constructed.

A blood from a patient (donor) suffering from rheumatoid arthritis is heparinized and introduced to the adsorber apparatus through blood inlet 9. The introduced blood is flowed to adsorber module 13 through conduits 10 and 12 by means of pump 11, and plasma separated by adsorber module 13 is collected through plasma outlet 16. With this adsorber apparatus, recycling of the blood is stably, sufficiently performed using an extracorporeal circuit blood volume as small as 210 ml. This volume is satisfactorily small from the viewpoint of attaining the whole blood treatment with a decreased extracorporeal circuit blood volume being taken outside the body. The amount of the collected plasma is measured. Further, the rheumatoid factor concentration of the collected plasma is determined in the same manner as in Example 1. The results are shown in Table 1.

As apparent from the results shown in Table 1, although the average inside diameters of the individual hollow fibers are different between the hollow fibers used in Examples 3 to 5, the surface areas of the hollow fibers in the prepared adsorber modules of Examples 3 to 5 are almost the same. However, the larger the L/D$^2$ value, the smaller the amount of rheumatoid factor in the treated blood becomes. On the other hand, the larger the L/D$^2$ value, the larger the collection rate of plasma becomes. This means that the smaller the inside diameter of the hollow fiber, the higher the efficiency of plasma separation becomes. Particularly, when the L/D$^2$ value is 2,000 mm$^{-1}$ or higher as in Examples 3 and 4, plasma separation can be conducted with extremely high efficiency.

TABLE 1

| Example | Winding rate (m/min) | Average inside diameter of hollow fiber (D, mm) | Average effective length of hollow fiber (L, mm) | L/D$^2$ (mm$^{-1}$) | Surface area of hollow fibers in adsorber module (m$^2$) | Separation rate of plasma (ml/min) | Amount of rheumatoid factor after the blood treatment |
|---|---|---|---|---|---|---|---|
| 3 | 300 | 0.340 | 250 | 2,200 | 110 | 21 | 160 |
| 4 | 600 | 0.280 | 250 | 3,200 | 100 | 27 | 80 |

TABLE 1-continued

| Example | Winding rate (m/min) | Average inside diameter of hollow fiber (D, mm) | Average effective length of hollow fiber (L, mm) | $L/D^2$ (mm$^{-1}$) | Surface area of hollow fibers in adsorber module (m$^2$) | Separation rate of plasma (ml/min) | Amount of rheumatoid factor after the blood treatment |
|---|---|---|---|---|---|---|---|
| 5 | 200 | 0.380 | 250 | 1,700 | 120 | 11 | 640 |

Condition: Blood flow rate is 50 ml/min (Ht = 35%) and the original amount of rheumatoid factor before the blood treatment is 1280.

COMPARATIVE EXAMPLE 1

An adsorber material comprising a granular carrier and tryptophan linked to the carrier is used for the adsorption of rheumatoid factor. The adsorber material is produced as follows.

A uniform mixture of 100 g of vinyl acetate, 64.3 g of triallyl isocyanurate, 100 g of ethyl acetate, 100 g of heptane, 7.5 g of polyvinyl acetate (degree of polymerization: 500) and 3.8 g of 2,2'-azobisisobutyronitrile, and 400 ml of an aqueous solution containing 1% by weight of polyvinyl alcohol, 0.05% by weight of sodium dihydrogenphosphate dihydrate and 1.5% by weight of sodium dihydrogenphosphate dodecahydrate are charged in a flask and sufficiently mixed by stirring. Then, the resultant mixture is heated, while stirring, successively at 65° C. for 18 hours and at 75° C. for 5 hours to conduct a suspension polymerization. The thus obtained granular copolymer is filtered off and washed with water. The thus obtained copolymer is subjected to acetone extraction. The resultant copolymer is subjected to ester exchange reaction at 40° C. for 18 hours in a solution of 46.5 g of sodium hydroxide in 2 l of methanol. The thus obtained gel of the copolymer has an average particle diameter of 100 μm, a vinyl alcohol unit (qOH) per unit weight of 8.9 meq/g, a specific surface area of 65 m$^2$/g and a cut-off molecular weight of $9 \times 10^5$ as measured using a dextran.

Then, 50 g of the obtained gel (dry basis) is suspended in 600 ml of dimethyl sulfoxide and to the resultant suspension are added 391.5 ml of epichlorohydrin and 50 ml of 30% (w/w) aqueous sodium hydroxide solution. The mixture is stirred at 30° C. for 5 hours to activate the gel.

After the gel activation, the resultant gel is washed successively with dimethylsulfoxide and with water, and suction-dehydrated. The thus obtained activated gel is suspended in 800 ml of 0.1M sodium carbonate buffer containing 8.15g of tryptophan. The suspension is stirred at 50° C. for 14 hours to link the tryptophan to the overall surface of the gel. Thereafter, to the mixture is added 165 ml of an aqueous tris(hydroxyethyl-)aminomethane solution having a tris(hydroxyethyl-)aminomethane concentration of 60.6 mg/ml. Then, the resultant mixture is heated at 50° C. for 5 hours while stirring so that the active groups of the gel remaining unlinked by tryptophan are blocked. The resultant gel is sufficiently washed with water, to thereby obtain an adsorber material. The amount of the tryptophan linked to the adsorber material is 360 μmol/g (dry basis).

Figure 5:
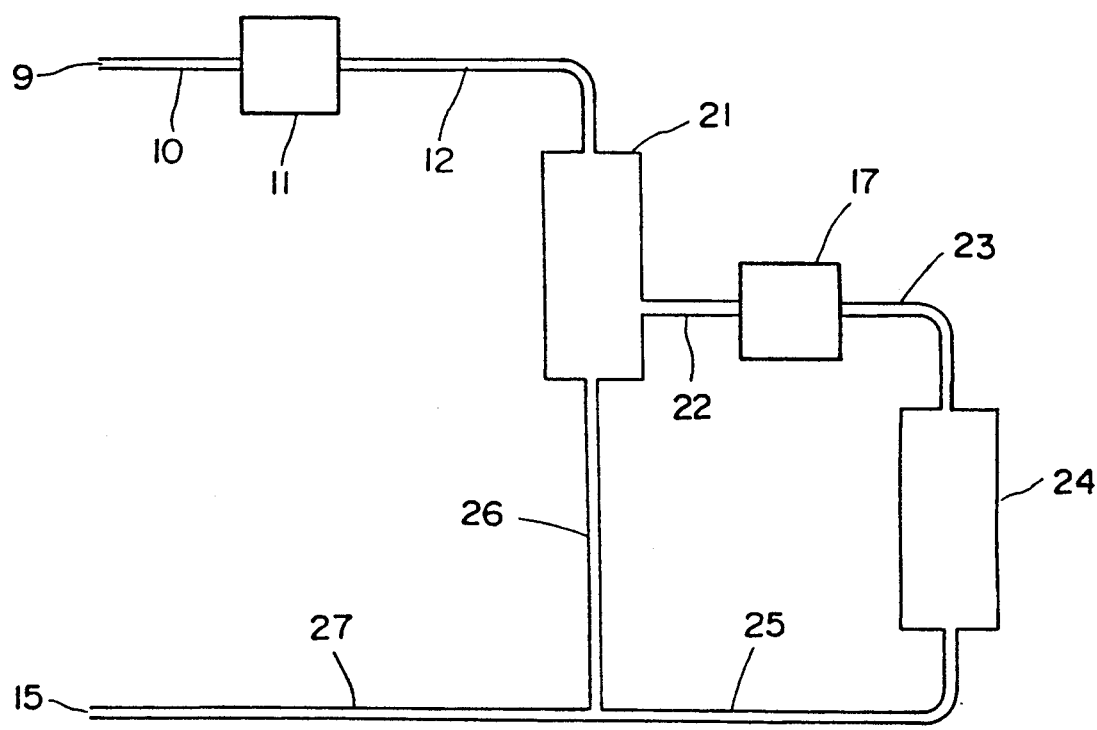
FIG. 5 is a diagrammatic view of a comparative adsorber apparatus.

The adsorber material is filled in a column having an inside diameter of 40 mm and a length of 318 mm to obtain an adsorber column. Using the adsorber column, an adsorber apparatus as shown in FIG. 5 is constructed. In FIG. 5, numeral 24 designates the adsorber column and numeral 21 designates a plasma separator. The adsorber column 24 is connected to the plasma outlet of plasma separator 21 through conduit 21, pump 17 and conduit 23 so that the plasma separated by plasma separator 21 can be conveyed to adsorber column 24 by means of pump 17. As the plasma separator, Plasmaflo ® AP05H manufactured and sold by Asahi Medical Co., Ltd., Japan is used.

A blood from a patient suffering from rheumatoid arthritis is heparinized. An aliquot of the blood is subjected to measurement of amount of rheumatoid factor by a passive hemagglutination test method using a RAHA test kit (manufactured and sold by Fuji Zoki Pharmaceutical Co., Ltd., Japan). The blood is introduced to the adsorber apparatus from the patient (donor) through blood inlet 9 and flowed to plasma separator 21 at a flow rate of 50 ml/min through conduits 10 and 12 by means of pump 11. The blood is separated into plasma and cell-enriched blood by plasma separator 21, and the plasma is flowed to adsorber column 24 through conduits 22 and 23 by means of pump 17 at a flow rate of 17 m/min. In conduit 27, the plasma treated with adsorber column 24 and flowed through conduit 25 is combined with cell-enriched blood flowed through conduit 26, and the resultant mixture is returned to the donor through blood outlet 15. The blood from the donor is recycled through the same adsorber apparatus. The recycling is continued for 30 min.

After the blood recycling for 30 min, an aliquot of the recycled blood is collected from blood outlet 27 and the amount of rheumatoid factor in the blood is measured in the same manner as in Example 1.

As a result, it is found that the amount of rheumatoid factor before the blood treatment which is 1280, is decreased to 160 after the blood treatment, which is comparable to the amount of the rheumatoid factor in the blood after the blood treatment conducted in Example 3. However, with this adsorber apparatus, recycling of the blood is performed using an extracorporeal circuit blood volume as large as 610 ml. This volume is disadvantageously very large so that a heavy burden is posed on the patient during the blood treatment.

What is claimed is:

1. An adsorber module for whole blood treatment comprising:
    a casing provided with blood introduction means and blood withdrawal means, and
    a plurality of porous hollow fibers substantially equal in length arranged substantially in parallel relationship and bonded together at both end portions thereof to form a bundle, each porous hollow fiber of said bundle having openings at both terminal ends thereof,
    said bundle being disposed in said casing along the length of said casing, said bundle being fluid-tightly connected to said casing,
    said both end portions of the hollow fibers of said bundle being fluid-tightly connected to said blood introduction means and said blood withdrawal means, respectively, thereby establishing fluid communication between said blood introduction means and said blood withdrawal means through said bundle of hollow fibers,
    each porous hollow fiber comprising a membranous porous resin matrix having pores which open at least at the inner wall of the hollow fiber and a plurality of ligands attached to the overall surface of said porous resin matrix, said overall surface being all of the inner and outer surfaces of the hollow fiber membrane and the surfaces defined by the walls of open pores present within the membranous porous resin matrix, said plurality of ligands having low antigenicity and interacting with a substance to be adsorbed, said plurality of porous hollow fibers having an average effective length (L mm) and an average inner diameter (D mm) which satisfy the inequality:

$$L/D^2 \,(\mathrm{mm}^{-1}) \geq 2000$$

said average effective length being defined as an average of the lengths of said plurality of porous hollow fibers minus the lengths of said both end portions of said bundle of porous hollow fibers at which the fibers are bonded together and fluid-tightly connected to said blood introduction means and said blood withdrawal means, respectively.

2. The module according to claim 1, wherein said plurality of ligands are linked to the overall surface of said porous resin matrix by covalent bonding.

3. The module according to claim 1, wherein said plurality of ligands are hydrophobic compounds.

4. The module according to claim 1, wherein said plurality of ligands are polyanions.

5. The module according to claim 1, wherein each said porous resin matrix has an average pore diameter of from 0.005 to 3 μm.

6. The module according to claim 5, wherein said average pore diameter is in the range of from 0.01 to 2 μm.

7. The module according to claim 1. wherein said membranous porous resin matrix of each hollow fiber has pores therewithin and openings on both surfaces thereof, said pores cooperating with said openings to form through-paths running between both the surfaces of said resin matrix.

8. The module according to claim 7, wherein said casing is further provided with means defining at least one opening for withdrawing plasma.

9. The module according to claim 1, wherein each said resin matrix is composed of at least one resin selected from the group consisting of cellulose, a cellulose derivative, a water-insoluble polyvinyl alcohol, a copolymer of ethylene and vinyl alcohol, a polyolefin, a polysulfone and a poly tetrafluoroethylene.

10. An adsorber apparatus for whole blood treatment consisting essentially of:
 (a) an adsorber module comprising:
  a casing provided with blood introduction means and blood withdrawal means, and
  a plurality of porous hollow fibers substantially equal in length arranged substantially in parallel relationship and bonded together at both end portions thereof to form a bundle, each porous hollow fiber of said bundle having openings at both terminal ends thereof,
  said bundle being disposed in said casing along the length of said casing, said bundle being fluid-tightly connected to said casing,
  said both end portions of the hollow fibers of said bundle being fluid tightly connected to said blood introduction means and said blood withdrawal means, respectively, thereby establishing fluid communication between said blood introduction means and said blood withdrawal means through said bundle of hollow fibers
  each porous hollow fiber comprising a membranous porous resin matrix having pores which open at least at the inner wall of the hollow fiber and a plurality of ligands attached to the overall surface of said porous resin matrix,
  said overall surface being all of the inner and outer surfaces of the hollow fiber membrane and the surfaces defined by the walls of open pores present within the membranous porous resin matrix,
  said plurality of ligands having low antigenicity and interacting with a substance to be absorbed,
  said plurality of porous hollow fibers having an average effective length (L mm) and an average inner diameter (D mm) which satisfy the inequality:

$$L/D^2 \,(\mathrm{mm}^{-1}) \geq 2000$$

said average length being defined as an average of the lengths of said plurality of porous hollow fibers minus the lengths of said both end portions of said bundle of porous hollow fibers at which the fibers are bonded together and fluid-tightly connected to said blood introduction means and said blood withdrawal means, respectively,
 (b) blood introducing passage means comprising a first conduit having one end fluid-tightly connected to said blood introduction means of module (a), a second conduit having a blood inlet at one end thereof, and a blood transport means disposed between and fluid-tightly connected to the other ends of said first and second conduits; and
 (c) blood withdrawing passage means comprising a third conduit having one end fluid-tightly connected to said blood withdrawal means of module (a) and having a blood outlet at the other end thereof.

11. The apparatus according to claim 10, wherein said membranous porous resin matrix of each hollow fiber of said adsorber module has pores therewithin and openings on both surfaces thereof, said pores cooperating with said openings to form through-paths running between both the surfaces of said resin matrix.

12. The apparatus according to claim 11, wherein said casing of module (a) is further provided with means defining at least one opening for withdrawing plasma, said at least one opening being fluid-tightly connected to said blood withdrawing passage means through a bypass comprising a fourth conduit having one end fluid-tightly connected to said at least one opening, a fifth conduit having one end fluid-tightly connected to said blood withdrawing passage at an intermediate position of said blood withdrawing passage, and plasma transport means disposed between and fluid-tightly connected to the other ends of said fourth and fifth conduits.

* * * * *